United States Patent [19]

Gregory et al.

[11] Patent Number: 5,453,495
[45] Date of Patent: Sep. 26, 1995

[54] DISAZO COMPOUNDS CONTAINING AN OPTIONALLY SUBSTITUTED PIPERAZINYL GROUP

[75] Inventors: Peter Gregory, Bolton; Ronald W. Kenyon, Failsworth; Prahalad M. Mistry, Ashton-Under-Lyne, all of United Kingdom

[73] Assignee: Zeneca Limited, London, England

[21] Appl. No.: 361,485

[22] Filed: Dec. 22, 1994

[30] Foreign Application Priority Data

Dec. 23, 1993 [GB] United Kingdom ............... 9326373

[51] Int. Cl.$^6$ ............... C09B 31/08; C09D 11/02
[52] U.S. Cl. ............... 534/728; 534/761; 534/797; 534/799; 534/599; 544/389; 544/395; 106/20 D; 106/22 K
[58] Field of Search ............... 534/761, 797, 534/728

[56] References Cited

U.S. PATENT DOCUMENTS 5,053,495  10/1991  Greenwood et al. ............... 534/728 X
5,125,969   6/1992  Nishiwaki et al. ............... 106/22

FOREIGN PATENT DOCUMENTS 2507996   8/1976  Germany ............... 544/395

*Primary Examiner*—Robert Gerstl
*Assistant Examiner*—Fiona T. Powers
*Attorney, Agent, or Firm*—Cushman Darby & Cushman

[57] ABSTRACT

A compound of Formula (1) and salts thereof:

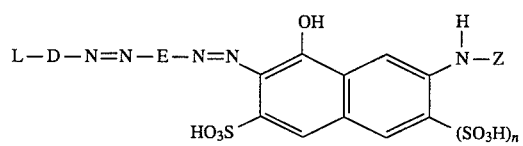

wherein:

L is optionally substituted piperazinyl;

D is optionally substituted phenylene or naphthylene;

E is optionally substituted phenylene, naphthylene or quinoline;

R is H or $C_{1-4}$-alkyl;

Z is optionally substituted carboxyaryl; and n has a value of 0 or 1.

A compound of Formula (1) is useful as a colorant for black inks suitable for ink jet printing.

8 Claims, No Drawings

DISAZO COMPOUNDS CONTAINING AN OPTIONALLY SUBSTITUTED PIPERAZINYL GROUP

This invention relates to a disazo compound and more particularly to a colorant suitable for the preparation of an aqueous ink for use in the production of a black image by ink jet printing.

For office ink jet printing (ijp) it is important that an image on plain paper exhibits a combination of good properties, especially, good light and water fastness. It is also important that the colorant has good solubility in the ink medium to minimise the risk of drying out in the nozzle of the printer and to permit the achievement of a strong image. The printing of a black image on a plain paper substrate is the most important requirement for office ijp and it is also important that black colorants should give a strong neutral black shade with minimal bronzing. The original ijp black colorants, such as CI Food Black 2 and CI Direct Black 168, generally had good aqueous solubility and light fastness but they had very poor water fastness. Although recent developments have led to colorants with improved water fastness this is still generally significantly below 100%, and the improvement has generally been at the expense of solubility and shade.

The present invention is concerned with colorants having a combination of properties which make them especially suitable for use in office ijp.

According to the present invention there is provided a compound of Formula (1) and salts thereof:

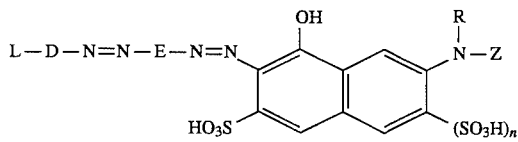

wherein:

L is optionally substituted piperazinyl;

D is optionally substituted phenylene or naphthylene;

E is optionally substituted phenylene, naphthylene or quinoline;

R is H or $C_{1-4}$-alkyl;

Z is optionally substituted carboxyaryl; and n has a value of 0 or 1.

The optionally substituted piperazinyl group L is preferably of the Formula (2):

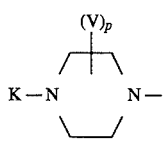

wherein:

K is H or optionally substituted alkyl, aryl, acyl or ester;

V is optionally substituted alkyl; and p is 0, 1 or 2.

When K or V is optionally substituted alkyl, the alkyl is preferably $C_{1-4}$-alkyl, such as methyl, ethyl, propyl or butyl, especially methyl, each of which may be substituted as hereinafter described.

When K is optionally substituted aryl, the aryl is preferably phenyl, which may be substituted as hereinafter described. When K is optionally substituted ester, the ester is preferably of formula —COOT or —$SO_3$T wherein T is optionally substituted alkyl or aryl, especially $C_{1-4}$-alkyl or phenyl, each of which may be substituted as hereinafter described. When K is optionally substituted acyl, the acyl is preferably formyl, alkyl- or aryl-carbonyl or alkyl- or arylsulphonyl, in which the alkyl is preferably $C_{1-4}$-alkyl and the aryl is preferably phenyl, each of which may be substituted as hereinafter described.

Examples of optionally substituted piperazin-1-yl groups represented by L are piperazin-1-yl, 4-hydroxyethylpiperazin-1-yl, 4-acetyl-piperazin- 1-yl, 3-methylpiperazin-1-yl, 3-methyl-4-acetylpiperazin- 1-yl, 4-formylpiperazin-1-yl and 4-methylpiperazin-1-yl.

D is preferably optionally substituted phen-1,3-ylene or phen-1,4-ylene, especially the latter.

When E is optionally substituted phenylene, the phenylene is preferably phen-1,4-ylene. When E is optionally substituted naphthylene, the naphthylene is preferably naphth-1,4-ylene. When E is optionally substituted quinolinylene, the quinolinylene is preferably quinolin-5,8-ylene, each of which may be substituted as hereinafter described.

Where E is substituted phenylene it is preferably of the Formula (2a):

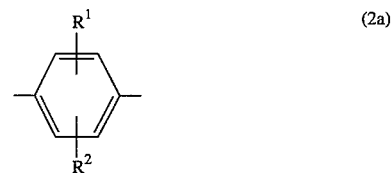

wherein $R^1$ is optionally substituted alkyl, optionally substituted alkoxy or $NR^3R^4$;

$R^2$ is H, halogen, —COOH, —$SO_3$H, optionally substituted alkyl, optionally substituted alkoxy or optionally substituted alkylthio;

$R^3$ is H or optionally substituted alkyl; and $R^4$ is H, optionally substituted alkyl or acyl.

Examples of substituted phenylene groups represented by E are 2-aminophen- 1,4-ylene, 2-amino-5-methoxyphen-1,4-ylene, 2-methylaminophen-1,4-ylene, 2-acetylaminophen-1, 4-ylene, 2,5-dimethoxyphen-1,4-ylene, 2-methoxy-5-methyl-phen-1,4-ylene, 2-methylphen-1,4-ylene, 2-methoxyphen- 1,4-ylene, 2-methoxy-5-acetylaminophen-1,4-ylene.

Where E is optionally substituted naphthylene it is preferably of the Formula (2b):

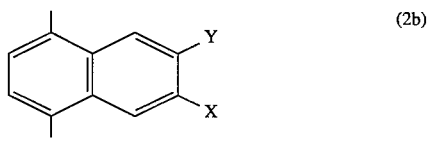

wherein each of X and Y is independently selected from —COOH, —$SO_3$H and H. In the group of Formula (2b) it is preferred that one of X and Y is COOH or $SO_3$H, especially the former and the other is H or that both X and Y are H.

R is preferably H or methyl but more especially H.

Z is preferably 2-, 3- or 4-carboxyphenyl or 2,4-, 3,4- or 3,5-dicarboxyphenyl, especially 3-carboxyphenyl, 4-carboxyphenyl or 3,5-dicarboxyphenyl, each of which may be further substituted as hereinafter defined but is preferably free from further substituents.

Where K, V, D, E or Z contains or represents a substituted alkyl or aryl group as hereinbefore described, each substituent on the alkyl or aryl group is preferably selected from $C_{1-4}$-alkyl; especially methyl or ethyl; $C_{1-4}$-alkoxy, especially methoxy or ethoxy; OH; CN; $NO_2$; —COOH; —$SO_3H$; amino; halogen, especially chloro or bromo; acylamino, especially $C_{1-4}$-alkylcarbonyl-amino, benzoylamino or ureido; ester, especially $C_{1-4}$-alkoxycarbonyl; acyl, especially $C_{1-4}$-alkylcarbonyl; and acyloxy, especially $C_{1-4}$-alkylcarbonyloxy; unless stated otherwise.

The group L—D— in Formula (1) is preferably of the Formula (3) or Formula (4) wherein m is 0 or 1.

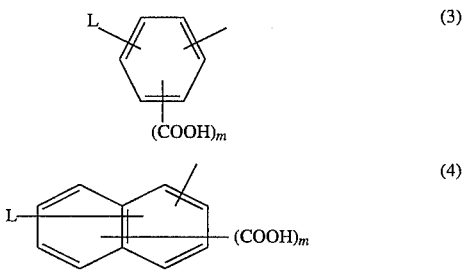

and especially of Formula (3) wherein m is 0 or 1 and L is of Formula (2) in which p is 0 or 1; V is $CH_3$ or $OCH_3$; and K is selected from H, $C_{1-4}$-alkyl, especially methyl; formyl; $C_{1-4}$-alkylcarbonyl; phenylcarbonyl; ester, especially $C_{1-4}$-alkoxycarbonyl or phenoxycarbonyl; hydroxy-$C_{1-4}$-alkyl, especially 2-hydroxyethyl.

A further feature of the present invention provides a compound of Formula (5) and salts thereof:

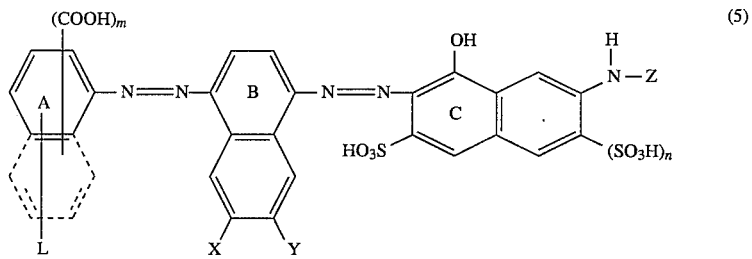

wherein:

L is of Formula (2);

W is C—H, C—COOH or N;

X is H, COOH or $SO_3H$;

Y is H, COOH or $SO_3H$; and

K, V, p, m, Z and n are as hereinbefore defined provided that (1) at least one of X and Y is H or COOH and (2) W is C—H or N when X and Y are both COOH.

Nucleus A may be a phenyl or naphthyl group, preferably the former and, where it is naphthyl, the substituents shown may be on either benzene ring. It is however preferred that Nucleus A is phenyl and that L is in the 2- or 4-position, especially the latter, with respect to the azo group. Where Nucleus A is phenyl and m is 1, the COOH group is preferably ortho with respect to L. In formulae (3) and (5) it is preferred that m is 1.

In Nucleus B, it is preferred that W is C—H or N, especially the former. It is also preferred that one of X and Y is COOH or $SO_3H$, especially the former and the other is H or that both X and Y are H.

In compounds of Formula (1) and (5) it is preferred that Z is 3-carboxyphenyl, 4-carboxyphenyl or 3,5-dicarboxyphenyl. It is also preferred that n is 0.

The compounds of Formula (1) and (5) preferably contain at least two carboxy groups. It is also preferred that the number of carboxy groups is equal to or greater than the number of sulpho groups.

Components from which Nucleus B may be derived include 1-naphthylamine, 1,6-Cleves acid, 1,7-Cleves acid, mixed Cleves acids, 8-amino-2-naphthoic acid and mixed 5-amino- and 8-amino-2-naphthoic acids. If such mixed components are employed the product will be a mixture of dyes containing different isomeric Nuclei B. Such mixtures can be made directly from mixed Cleves acids or from the mixed isomers of 5-amino-2-naphthoic acid and 8-amino-2-naphthoic acid, respectively, without the need to separate the isomers.

Components from which Nucleus C may be derived include N-(4-carboxyphenyl)-Gamma acid, N-methyl-N-(4-carboxyphenyl)-Gamma acid, N-(3-carboxyphenyl)-Gamma acid and N-(3,5-dicarboxyphenyl)-Gamma acid.

According to a further feature of the invention there is provided an intermediate of the Formula (6):

L—D—$NH_2$ (6)

wherein L and D are as hereinbefore defined.

Examples of intermediates of Formula (6) include 3-carboxy-4-(4'-hydroxyethylpiperazinyl)aniline, 3-carboxy-4-piperazinylaniline, 4-(4'-methylpiperazinyl)aniline, 4-[(4'-acetyl-piperazinyl)-3-carboxy-aniline, 4-[(4'-acetyl-3'-methyl-piperazinyl)-3-carboxyaniline, 4-[(4'-formylpiperazinyl)aniline and 4-[(3'-methylpiperazinyl)-3-carboxyaniline.

The compounds of Formula (1) and (5) can be made by analogous processes to those described in EP 356080A. For example a compound of Formula (6) may be diazotised, e.g. in water at 0°–5° C. using $NaNO_2$ and acid, coupled onto an amine of formula H—E—$NH_2$ to give a monoazo compound, the monoazo compound may then be diazotised in a similar manner and coupled onto a suitable 1-hydroxy-3-sulpho compound having an —NHZ substituent at the 7-position and optionally a sulpho group at the 6-position; wherein E, Z and the compound of Formula (6) are as hereinbefore defined. In the compound of Formula (6) the group L may be protected by acylating the free N atom in the piperazinyl group to form an acylpiperazinyl group. Suitable processes are substantially as described in the Examples.

The compound of Formula (6) can be prepared by reacting a piperazine, L—H, where L is as defined in Formula (2), with a compound Cl—D—$NO_2$, where D is as herebefore defined, in an aqueous medium at a temperature from 50°–100° C., preferably from 80°–95° C. for up to 24 hours, preferably in the presence of an acid binding agent, such as NaOH, Na$_2$CO$_3$ or NaHCO$_3$, to give a compound L—D—N)$_2$ and reducing the NO$_2$ group, e.g. by hydrogenation. Examples of the compound Cl—D—NO$_2$ are 4-chloronitrobenzene, 2-chloro-5-nitro-benzoic acid, 3-nitro-4-chloro benzoic acid, 1-nitro-4-chloronaphthalene, 1-nitro-5-chloronaphthalene and 1-nitro-4-chloro-7-carboxy-naphthalene.

A compound of Formula (1) or Formula (5), hereinafter referred to as a Colorant, is notable for its strong, neutral, black shade, fastness to water and light and good solubility in water. Compositions of the Colorant with water-miscible organic solvents, especially such compositions contained in an aqueous medium, are characterised by a low tendency to bronze when printed on paper.

The Colorant is especially useful for the preparation of an ink, especially an aqueous ink suitable for use in ink jet printing, especially thermal ink jet printing.

The Colorant is preferably a salt of a compound of Formula (1) or Formula (5), especially a salt with an alkali metal cation or optionally substituted ammonium cation or a mixture of such cations. An especially preferred Colorant is a salt with ammonia or a substituted ammonium ion or a mixture thereof.

The substituted ammonium cation may be a quaternary ammonium cation of the formula $^+$NQ$_4$ in which each Q independently is an organic radical, or two or three Qs together with the nitrogen atom to which they are attached form a heterocyclic ring and all remaining Qs are selected from C$_{1-4}$-alkyl. Preferred organic radicals represented by Q are C$_{1-4}$-alkyl, especially methyl and C$_{1-4}$-hydroxyalkyl, especially hydroxyethyl. Preferred heterocyclic rings formed by NQ$_4$ are 5 or 6 membered heterocyclic rings.

Examples of quaternary ammonium groups of formula $^+$NQ$_4$ are N$^+$(CH$_3$)$_4$, N$^+$(CH$_2$CH$_3$)$_4$, N-methylpyridinium, N,N-dimethylpiperidinium and N,N-dimethylmorpholinium.

Alternatively the substituted ammonium cation may be of the formula $^+$NHT$_3$ wherein each T independently is H, C$_{1-4}$-alkyl or hydroxy-C$_{1-4}$-alkyl provided at least one T is C$_{1-4}$-alkyl, or two or three groups represented by T together with the nitrogen atom to which they are attached form a 5 or 6 membered ring, especially a pyridine, piperidine or morpholine ring. It is preferred that the substituted ammonium cation is derived from an amine which is volatile under ambient conditions, i.e. at 20° C. and atmospheric pressure.

Examples of groups of formula $^+$NHT$_3$ are (CH$_3$)$_3$N$^+$H, (CH$_3$)$_2$N$^+$H$_2$, H$_2$N$^+$(CH$_3$)(CH$_2$CH$_3$), CH$_3$N$^+$H$_3$, CH$_3$CH$_2$N$^+$H$_3$, CH$_3$CH$_2$CH$_2$N$^+$H$_3$, (CH$_3$CH$_2$)$_2$N$^+$H$_2$, (CH$_3$CH$_2$)$_3$N$^+$H, (HOCH$_2$CH$_2$)$_3$N$^+$H, (CH$_3$)$_2$CHN$^+$H$_3$, pyridinium, piperidinium and morpholinium.

It is especially preferred that the Colorant is in the form of the ammonium salt or the mono-, di- or tri- methyl- or ethyl-ammonium salt.

The ammonium salt form of the Colorant can be prepared by dissolving an alkali metal salt of the Colorant in water, acidifying with a mineral acid, adjusting the solution to pH 9–9.5 with ammonia or the appropriate amine and removing alkali metal salt by dialysis.

The water-fastness of the Colorant on paper may be increased by printing it from an aqueous medium in the form of ammonium or substituted ammonium salts.

According to a further feature of the present invention there is provided an ink comprising a Colorant and a liquid medium. It is preferred that the compound is completely dissolved in the liquid medium to form a solution.

The ink preferably contains from 0.5% to 20%, more preferably from 0.5% to 15%, and especially from 1% to 5%, by weight, of the Colorant based on the total weight of the ink.

The liquid medium is preferably water or a mixture comprising water and one or more water-soluble organic liquid, the water and organic liquid(s) preferably being in a weight ratio from 99:1 to 50:50 and more preferably 95:5 to 60:40 and especially 95:5 to 80:20.

The water-soluble organic liquid is preferably a C$_{1-4}$-alkanol such as methanol, ethanol, n-propanol, isopropanol, n-butanol, s-butanol, t-butanol or i-butanol; an amide such as dimethylformamide or dimethylacetamide; a ketone or ketone alcohol such as acetone or diacetone alcohol; an ether such as tetrahydrofuran or dioxane; an oligo- or poly-C$_{2-6}$-alkylene glycol such as diethylene glycol, triethylene glycol, poly(ethyleneglycol) or poly(propylene-glycol) of molecular weight up to 500; an alkylene glycol or thioglycol containing a C$_{2-6}$-alkylene group such as ethylene glycol, propylene glycol, butylene glycol, 1,5-pentanediol or hexylene glycol; a thiodiglycol; a polyol such as glycerol or 1,2,6-hexanetriol; a C$_{1-4}$-alkyl ether of a C$_{2-4}$-alkylene glycol or oligo-C$_{2-4}$-alkylene glycol such as 2-methoxyethanol, 2-(2-methoxy-ethoxy)ethanol, 2-(2-ethoxyethoxy)-ethanol, 2-[2-(2-methoxyethoxy)ethoxy]-ethanol, 2-[2-(2-ethoxyethoxy)-ethoxy]-ethanol or 2-[2-butoxy-ethoxy]ethanol; a heterocyclic ketone or sulphone, such as 2-pyrrolidone, N-methyl-2-pyrrolidone or sulpholane; or a mixture containing two or more of the aforementioned water-soluble organic solvents.

Preferred water-soluble organic solvents are selected from 2-pyrrolidone, N-methylpyrrolidone, sulpholane, C$_{2-6}$-alkylene glycols and C$_{1-4}$-alkylethers of polyhydric alcohols, such as ethylene glycol, diethylene glycol, triethylene glycol or 2-methoxy-2-ethoxy-2-ethoxyethanol; and a polyethylene glycol with a molecular weight of up to 500. A preferred specific solvent mixture is a binary or tertiary mixture of water and diethylene glycol; water and 2-pyrrolidone; water, ethylene glycol and 2-pyrrolidone; or water, ethylene glycol and N-methylpyrrolidone in weight ratios as herein described.

The water soluble organic solvent generally promotes the solubility of the Colorant in the aqueous medium and also the penetration of the Colorant into the substrate during printing. The addition of surfactants and/or biocides is also beneficial.

Examples of other suitable liquid media are given in U.S. Pat. Nos. 4,963,189, 4,703,113, 4,626,284 and EP 425150A.

It is preferred that the inks of the present invention comprise one or more penetrants, such as the water-soluble organic solvents hereinbefore described, to assist permeation of the dye into a paper substrate, a kogation-reducing agent to prevent or reduce the build-up of residue (koga) on the resistor surface in thermal ink jet printers and a buffer such as sodium borate, to stabilise the pH of the ink.

The kogation-reducing agent is preferably an oxo anion, such as described in EP 425150A The oxo-anion may be C$_2$O$_4^{2-}$, SO$_3^{2-}$, SO$_4^{2-}$, molybdate, or AsO$_4^{3-}$ but is preferably a phosphate ester or, diorganophosphate or more especially a phosphate salt such as a dibasic phosphate (HPO$_4^{2-}$), a monobasic phosphate (H$_2$PO$_4^-$) or a polyphosphate (P$_2$O$_7^{4-}$). The selection of counter ion is not believed to be critical and suitable examples include alkali metals, ammonium and alkylammonium cations. The kogation-reducing agent is preferably present in the ink at a concentration from 0.001% to 15% by weight of oxo-anion based on the total ink, and more preferably from 0.01% to 1%.

A further aspect of the present invention provides a process for printing a substrate with an ink using an ink jet printer, characterised in that the ink contains a Colorant as hereinbefore defined.

A suitable process for the application of an ink as hereinbefore defined comprises forming the ink into small droplets by ejection from a reservoir through a small orifice so that the droplets of ink are directed at a substrate. This process is commonly referred to as ink jet printing, and the ink jet printing processes for the present inks may be piezoelectric ink jet printing or thermal ink jet printing. In thermal ink jet printing, programmed pulses of heat are applied to the ink by means of a resistor, adjacent to the orifice during relative movement between the substrate and the reservoir.

A preferred substrate is an overhead projector slide or a cellulosic substrate, especially plain paper, which may have an acid, alkaline or neutral character. Textile materials such as cotton, viscose, jute, hemp, flax, nylon etc may also be printed with the Colorant if so desired, for example using the methods described in EP 550872A, (claims 1 to 9).

The preferred ink used in the process is as hereinbefore described. According to a still further aspect of the present invention there is provided a paper or an overhead projector slide printed with a Colorant as hereinbefore defined.

It has been found that further useful effects can be obtained if an ink containing the Colorant also contains a different dye, especially of the type disclosed for ink jet printing in EP 468647A; EP 468648A; EP 468649A and EP 559309A. Such a dye, especially a yellow dye from EP 468647A or a cyan dye from EP 559309A or a combination thereof, can assist in the suppression of any tendency to bronzing. The Colorant may be used in admixture with up to about 20% by weight of such dyes but more preferably from 2% to 10%, based on the weight of the resulting composition.

The invention is further illustrated by the following Examples in which all parts and percentages are by weight unless otherwise indicated.

EXAMPLE 1

Preparation of the dye of Formula

0°–10° C. for 2 hours and excess HNO₂ destroyed by the addition of a little sulphamic acid to give a diazo solution.

1-Naphthylamine (14.3 g) was dissolved in ethanol (200 ml) and the solution was added to the above diazo solution at 0°–10° C. The pH was adjusted to 3 by addition of 2N NaOH solution and the mixture stirred for 18 hours. The product of Formula (8) was filtered off, washed with water and dried at 60° C.

(b) Disazo Stage

The product of Formula (8) from Stage (a) (24.5 g) was dissolved in water (500 ml) at pH 8. NaNO₂ (3.0 g) was added and the solution added to a stirred mixture of ice water (100 ml) and conc HCl (15 ml). It was stirred at 0°–10° C. for 2 hours and excess HNO₂ in the diazo solution destroyed by adding a little sulphamic acid.

4-Carboxyphenyl-Gamma acid (15.0 g) was dissolved in water (400 ml) at pH 8 and the solution stirred and cooled to 0°–10° C.

The above diazo solution was then added at 0°–10° C. maintaining the pH at 8–9 by addition of 2N NaOH solution and stirred for 18 hours. The product of Formula (7) (ammonium salt) was precipitated by addition of 25% NH₄Cl, filtered, washed and dried. When made into an ink (2% in 92.5:7.5 water:2-pyrrolidone) and applied to plain paper using a thermal ink jet printer, the image had an intense black shade, very high water-fastness and good light fastness within 30 minutes after application to the paper.

The 5-amino-2-(4'-acetylpiperazinyl)benzoic acid used in Stage (a) was prepared by the following three stage process.

(1) Condensation

2-Chloro-5-nitrobenzoic acid (201 g) was dissolved in water (850 ml) by addition of Na₂CO₃. To the solution was added piperazine hexahydrate (600 g) and the mixture stirred and heated at 85°–90° C. for 18 hours. The resulting Solution was neutralised to pH 7 with conc HCl and allowed to cool to 20° C. The precipitated product was filtered, dried at 60° C. and recrystallised from hot water.

(2) Acetylation

The product from Stage (1) (127 g) was dissolved in water (1 liter) by the addition of 47% NaOH solution to a pH >7.

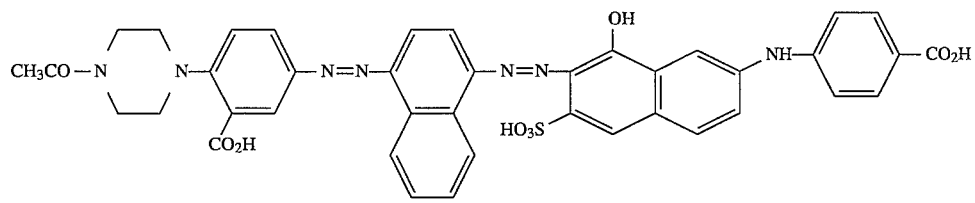

(7)

(a) Monoazo Stage

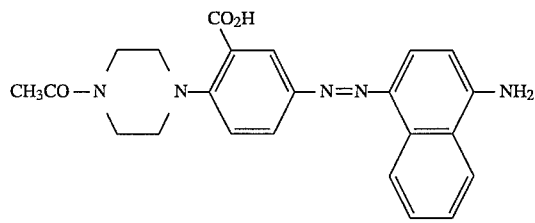

(8)

5-Amino-2-(4'-acetylpiperazino)benzoic acid (26.4 g) was added to a mixture of water (500 ml) and conc HCl acid (30 ml). The mixture was cooled to 0°–10° C. and NaNO₂ (6.9 g) added over 10 minutes. The mixture was stirred air To this solution was added acetic anhydride (200 ml) and the mixture stirred at 20°–25° C. for 1 hour. The precipitated product was filtered, washed with water and dried.

(3) Reduction

The product from Stage (2) was dissolved in water by the addition of 47% NaOH to raise the pH to 8–9. After carbon screening, 5% Pd/C catalyst was added and the mixture hydrogenated at 50°–60° C. and atmospheric pressure until H₂ uptake ceased. After screening to remove the catalyst, the product was precipitated by the addition of 2N HCl and isolated by filtration, washing with water and drying.

EXAMPLE 2

Preparation of the dye of Formula (9)

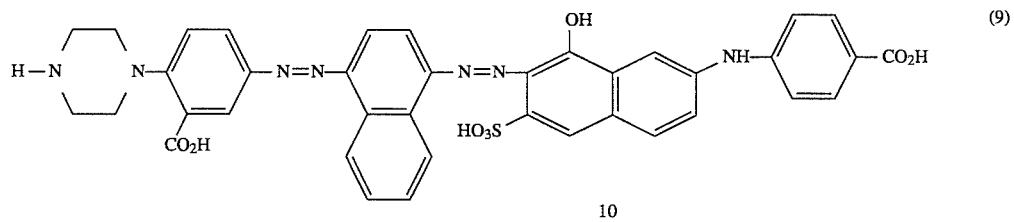
(9)

The product of Formula (7) from Example 1 was added to a mixture of 2N NaOH solution (800 ml) and ethanol (200 ml) and then heated at 70°–80° C. for 3 hours. The pH was adjusted to 5 with conc HCl and the precipitated product of Formula (9) (Na salt) filtered off and washed with 10% NaCl solution.

The product of Formula (9) (Na salt) was converted to the ammonium salt by dissolving in water (400 ml) at pH 9 and acidification to pH 1 with HCl. The product of Formula (9) (free acid), was filtered, reslurried in water and the pH adjusted to 9–10 with $NH_4OH$. The solution was dialysed to remove $Cl^-$ ions, screened and the water evaporated to give the same product as ammonium salt. This material had very good solubility in water (>10% at 25° C.) and, when made into an ink (2% in 92.5:7.5 water:2-pyrrolidone) and applied to plain paper using a thermal ink jet printer, the image had an intense black shade, very high water-fastness and good light fastness, within 30 minutes of application to the paper. Salts of this dye with various substituted ammonium ions including methylammonium, dimethylammonium, triethylammonium and triethanolammonium generally showed improved solubility in the ink medium and provided inks (2% dye in the above ink medium) which gave strong black images with good light and water fastness.

EXAMPLE 3

Preparation of the dye of Formula

EXAMPLE 4

Preparation of the dye of the formula (10)

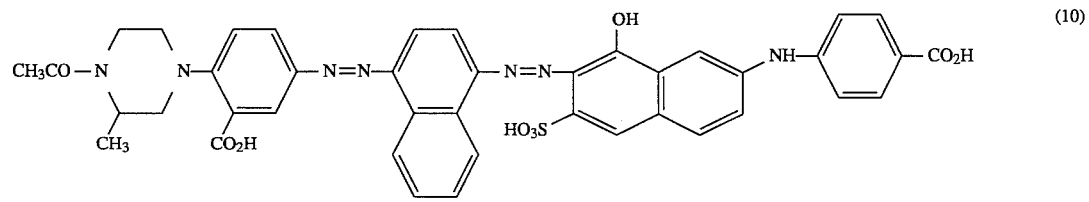
(10)

(a) Monoazo Stage

The method of Example 1, Stage (a), was followed except that in place of 5-amino-2-(4'-acetylpiperazino)benzoic acid (26.4 g) there was used 5-amino-2-(4'-acetyl-3'-methylpiperazino)benzoic acid (27.7 g).

(b) Disazo Stage

The method of Example 1, Stage (b) was followed except that in place of the monoazo product from Example 1, Stage (a), the monoazo product from Example 3, Stage (a), was used. The product of Formula (10) (free acid) was converted to the ammonium salt, dialysed, screened and evaporated to remove water.

The final product of Formula (10) (ammonium salt) showed good solubility in water and, when made into an ink (2% in 92.5:7.5 water:2-pyrrolidone) and applied to plain paper using a thermal ink jet printer, gave an intense black image with very high water fastness and good light fastness.

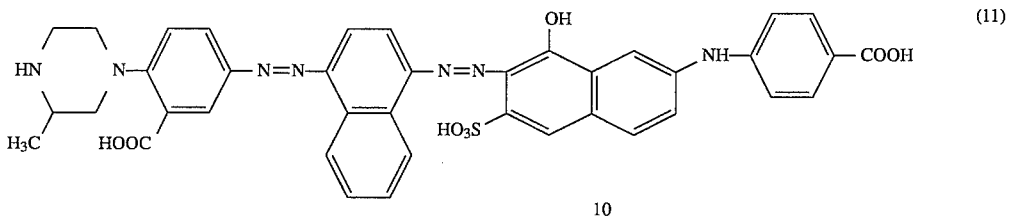

(11)

into plain paper using a thermal ink jet printer, gave a strong black image with excellent water fastness and good light fastness.

EXAMPLE 5

Preparation of the dye of Formula (12)

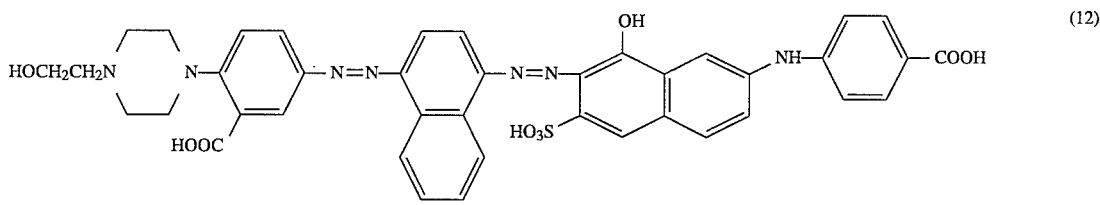

(12)

(a) Monoazo Stage

The method of Example 1, Stage (a) was followed except that in place of 5-amino-2-(4'-acetylpiperazino)benzoic acid (26.4 g) there was used 5-amino-2-(4'-(2'-hydroxyethyl)-piperazino)benzoic acid (26.5 g).

(b) Disazo Stage

The method of Example 1, Stage (b) was followed except that in place of the monoazo product from Example 1, Stage (a), the monoazo product from Example 5, Stage (a) was used. The compound of Formula (12) was converted into the dry ammonium salt as described in Example 2. When made into an ink (2.5% in water:2-pyrrolidone 90:10) and printed onto plain paper Using a thermal ink jet printer it gave an intense black image with excellent water fastness and good light fastness.

EXAMPLE 6

Preparation of the dye of Formula (13)

The method of Example 1, Stage (a) was followed except that in place of the 5-amino-2-(4'-acetylpiperazino)benzoic acid (26.4 g) there was used 5-amino-2-(4'-methylpiperazino)benzoic acid (23.5 g).

(b) Disazo Stage

The method of Example 1, Stage (b) was followed except that in place of the monoazo product from Example 1, Stage (a), the monoazo product from Example 6, Stage (a) was used. The product of Formula (13) was converted to the dry ammonium salt as described in Example 2. When made into an ink (2.5% in water:2-pyrrolidone 90:10) and printed onto plain paper using a thermal ink jet printer the product gave a strong black image with excellent waterfastness and good light fastness.

EXAMPLE 7

Preparation of the dye of Formula (14).

(13)

[structure of Formula (13)]

(a) Monoazo Stage

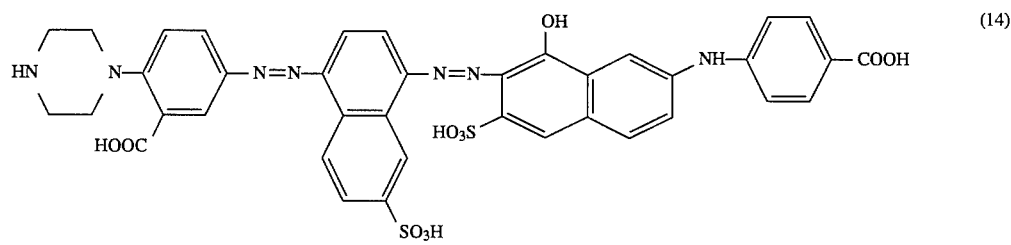

(a) Monoazo Stage Formula (15)

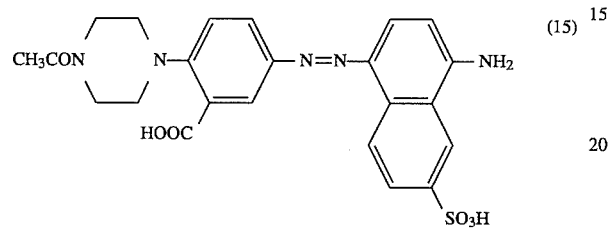

5-amino-2-(4'-acetylpiperazino)benzoic acid (26.4 g) was added to a mixture of water (500 ml) and HCl (30 ml). The mixture was cooled to 0°–10° C. and NaNO2[(6.9 g) added over 10 minutes. The mixture was stirred at 0°–10° C. for 2 hours and excess $HNO_2$ removed by addition of a little sulphamic acid% to leave a solution of the monoazo compound of Formula (15).

1-Aminonaphthalene-7-sulphonic acid (23.0 g) was dissolved in water (500 ml) by addition of 2N NaOH solution to pH 8. This solution was added to the above diazo solution at 0°–10° C., the pH adjusted to 3 with 2N NaOH solution and stirred for 18 hours. The product was filtered, washed with 20% NaCl solution and dried at 60° C.

(b) Disazo Stage (Formula (16))

disazo dye of Formula (16) from Example 7, Stage (b). The final product of Formula (14) was converted into the dry ammonium salt as described in Example 2. When made into an ink (2.5% in water:2-pyrrolidone 90:10) and printed onto plain paper using a thermal ink jet printer it gave a black image having very high waterfastness and good light fastness.

EXAMPLE 8

Preparation of the dye of Formula (17)

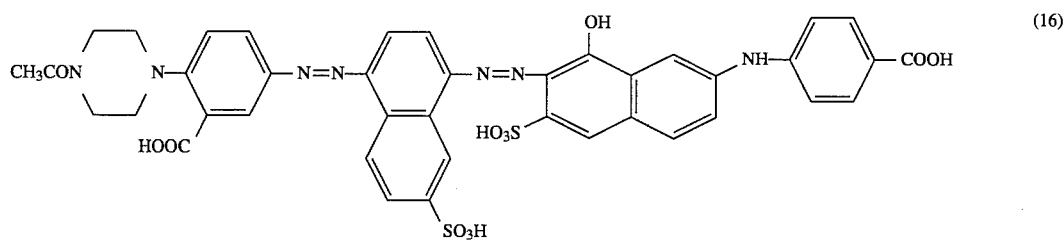

The method of Example 1, Stage (b) was followed except that in place of the monoazo product form Example 1, Stage (a), the monoazo compound of Formula (15) from Example 7, Stage (a) was used.

(c) Hydrolysis Stage

The method of Example 2 was followed except that in place of the disazo dye used in Example 2 there was used the

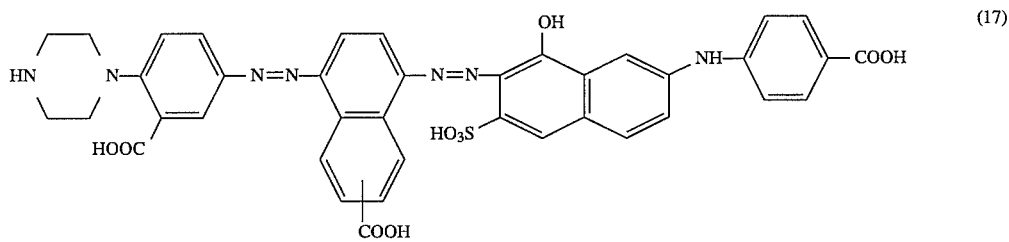

(17)

(a) Monoazo Stage

The method of Example 7, Stage (a) was followed except that in place of the 5-amino-2-(4'-acetylpiperazino)benzoic acid (26.4 g) there was used 5-amino-2-piperazino-benzoic acid (22.1 g) and in place of the 1-aminonaphthalene-7-sulphonic acid (23.0 g) there was used an approximately 50:50 mixture of 8-amino-2-naphthoic acid and 8-amino-2-naphthoic acid (18.7 g).

(b) Disazo Stage

The method of Example 1, Stage (b) was followed except that in place of the monoazo product from Example 1, Stage (a), the monoazo product from Example 8, Stage (a) was used. The product of Formula (17) was converted to the dry ammonium salt by the method of Example 2. When made into an ink (2.5% in water:2-pyrrolidone, 90:10) and printed onto plain paper using a thermal ink jet printer it gave a strong black image with excellent waterfastness and good light fastness.

EXAMPLE 9

Preparation of the dye of Formula (18)

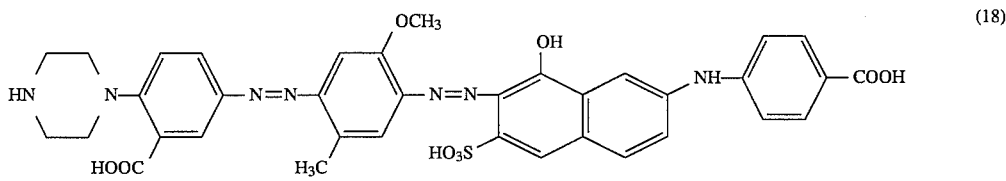

(19)

The method of Example 1, Stage (a) was followed except that in place of 1-naphthalamine (14.3 g) there was used 2-methoxy-5-methylaniline (13.7 g).

(b) Disazo Stage (Formula of (20))

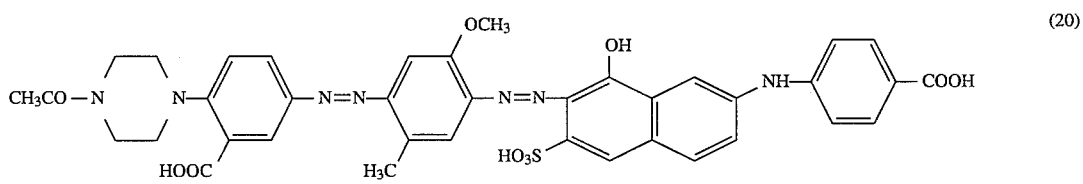

(18)

(a) Monoazo Stage (Formula (19))

(20)

The method of Example 1, Stage (b) was followed except that in place of the monoazo product from Example 1, Stage (a), the monoazo product of Formula (19) from Example 8, Stage (a) was used.

(c) Hydrolysis Stage

The method of Example 2 was followed except that in place of the disazo dye used in Example 2 there was used the disazo dye of the Formula (20) from Example 8, Stage (b). The product of Formula (18) was converted to the dry ammonium salt by the method of Example 2. When made into an ink (2.5% in 90:10 water:diethylene glycol) and printed onto plain paper it gave a black image having high waterfastness and good light fastness.

EXAMPLE 10

Preparation of the dye of Formula (21)

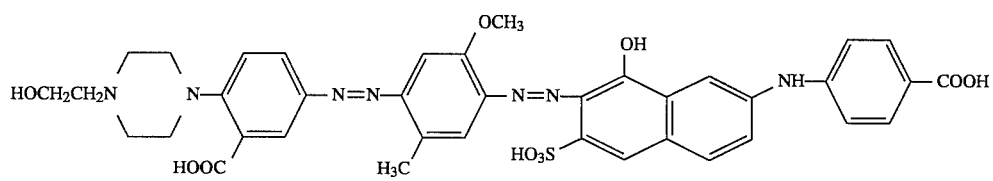

(a) Monoazo Stage

The method of Example 5, Stage (a), was followed except that in place of 1-naphthylamime (14.3 g) there was used 2-methoxy-5-methylaniline (13.7 g).

(b) Disazo Stage

The method of Example 1, Stage (b) was followed except that in place of the monoazo product from Example 1, Stage (a), the monoazo product from Example 10, Stage (a) was used. The compound of Formula (21) was converted to the dry ammonium salt by the method given in Example 2. When made into an ink (2.5% in 90:10 water:2-pyrrolidone) and printed onto plain paper using a thermal ink jet printer it gave a black image with very high water fastness and good light fastness.

EXAMPLE 11

Preparation of the Dye of the Formula (22)

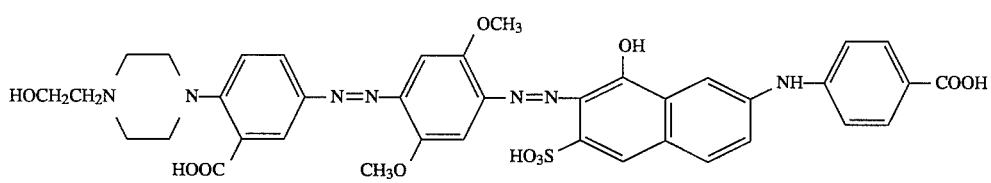

(a) Monoazo Stage

The method of Example 5, Stage (a) was followed except that in place of 1-naphthylamine (14.3 g) there was used 2,5-dimethoxyaniline (15.3 g).

(b) Disazo Stage

The method of Example 1, Stage (b) was followed except that in place of the monoazo product from Example 1, Stage (a), the above monoazo product from Example 11, Stage (a) was used. The compound of Formula (22) was converted to the dry ammonium salt by the method of Example 2. When made into an ink (2.5% in water:diethylene glycol 90:10) and printed onto plain paper using a thermal ink jet printer it gave a black image with high waterfastness and good light fastness.

EXAMPLE 12

Preparation of the dye of Formula 23)

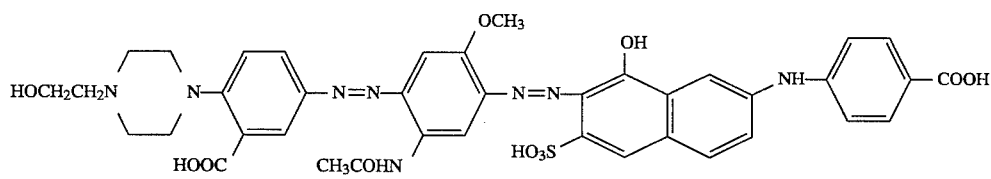

(a) Monoazo Stage

The method of Example 5, Stage (a) was followed except that in place of 1-naphthylamine (14.3 g) there was used 3-amino-4-methoxy-acetanilide (18.0 g).

(b) Disazo Stage

The method of Example 1, Stage (b) was followed except that in place of the monoazo product from Example 1, Stage (a), the monoazo product from Example 12, Stage (a) was used. The compound of Formula (23) was converted to the dry ammonium salt by the method of Example 2. When made into an ink (2.5% in water:2-pyrrolidone 90:10) and printed onto plain paper using a thermal ink jet printer it gave a black image with very high waterfastness and good light fastness.

EXAMPLE 13

Preparation of the dye of Formula (24)

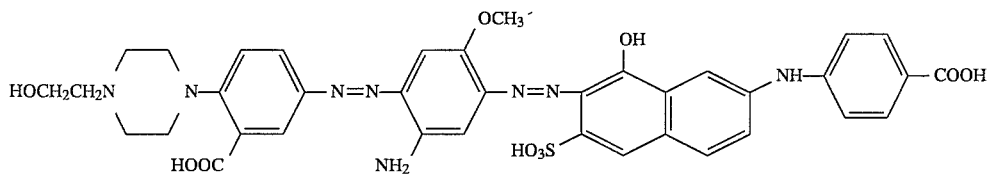

The product prepared as in Example 12 (10.0 g) was added to 2N NaOH solution (250 ml) and the solution stirred at 70°–80° C. for 2 hours. The mixture was acidified with conc HCl to pH 6 and the precipitated product filtered and washed with saturated NaCl solution. The product of Formula (24) was converted to the dry ammonium salt by the method of Example 2. When made into an ink (2.5% in 90:10 water:diethylene glycol) and printed onto plain paper using a thermal ink jet printer it gave a neutral black image with very high waterfastness and good light fastness.

EXAMPLE 14

Preparation of the dye of Formula (25)

(a) Monoazo Stage

The method of Example 5, Stage (a) was followed except that in place of 1-naphthylamine (14.3 g) there was used 3-ureidoaniline (15.2 g).

(b) Disazo Stage

The method of Example 1, Stage (b) was followed except that in place of the monoazo product form Example 1, Stage (a), the monoazo product from Example 14, Stage (a) was used. The compound of formula (25) was converted to the dry ammonium salt by the method described in Example 2. When made into an into an ink (2.5% in 90:10 water:diethylene glycol) and printed onto plain paper using a thermal ink jet printer it gave a black image having excellent waterfastness and good light fastness.

EXAMPLE 15

Preparation of the dye of Formula (26)

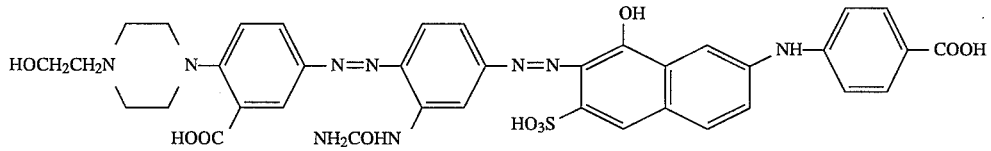

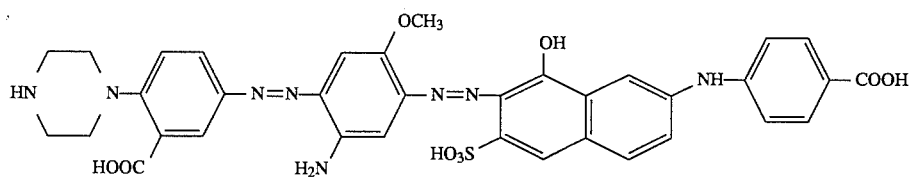

(a) Monoazo Stage (Formula (27))

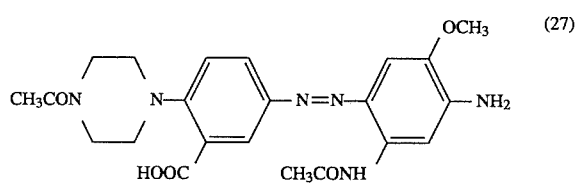

The method of Example 1, Stage (a) was followed except that in place of 1-naphthylamine (14.3 g) there was used 3-amino-4-methoxy-acetanilide (20.0 g).

(b) Disazo Stage (Formula (28))

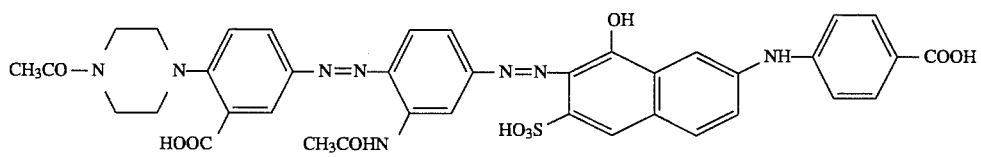

The method of Example 1, Stage (b) was followed except that in place of the monoazo product from Example 1, Stage (a), the monoazo compound of Formula 27 form Example 15, Stage (a) was used.

(c) Hydrolysis Stage

The method of Example 2 was followed except that in place of the dyestuff from Example 1 there was used the disazo dyestuff of Formula (28) from Example 15, Stage (b). The product of Formula (26) was converted to the dry ammonium salt by the method of Example 2. When made into an ink (2.5% in water:2-pyrrolidone 90:10) and printed onto plain paper using a thermal ink jet printer it gave a black image having very high waterfastness and good light fastness.

EXAMPLE 16

Preparation of the dye of the Formula

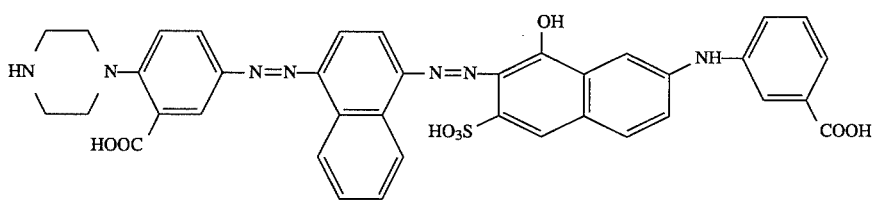

(a) Monoazo Stage 5-amino-2-(4'-piperazino)benzoic acid (18.0 g) was added to a mixture of water (300 ml) and conc. HCl (25 ml). The mixture was cooled to 0°–10° C. and NaNO$_2$ (5.6 g) added over 10 minutes. The mixture was stirred at 0°–10° C. for 2 hours and excess HNO$_2$ removed by addition of a little sulphamic acid.

1-Naphthylamine (11.6 g) was dissolved in ethanol (300 ml) and the solution added to the above diazo solution at 0°–10° C. The pH was adjusted to 4 by addition of 2N NaOH solution and the mixture stirred for 18 hours. The product was filtered, washed with water and dried.

(b) Disazo Stage

The method of Example 2 was followed except that in place of the monoazo product from Example 1, Stage (a), the monoazo product from Example 16, Stage (a) was used and in place of the 4-carboxyphenyl-gamma acid there was used 3-carboxyphenyl-gamma acid.

The compound of Formula (29) was converted to the dry ammonium salt as described in Example 2. When made into an ink (2.5% in 90:10 water:2-pyrrolidone and printed onto plain paper using a thermal ink jet printer it gave a black image with excellent waterfastness and good light fastness.

EXAMPLE 17

Preparation of the dye of the Formula

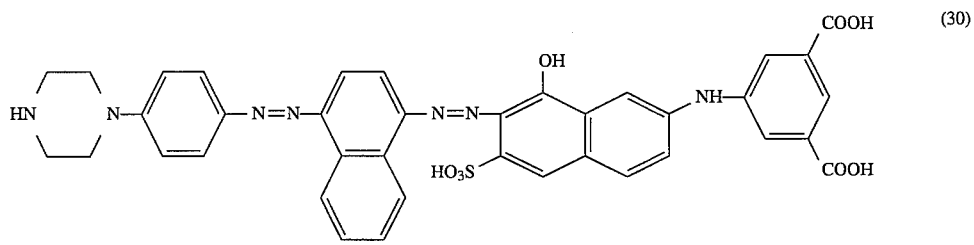
(30)
(a) Monoazo Stage
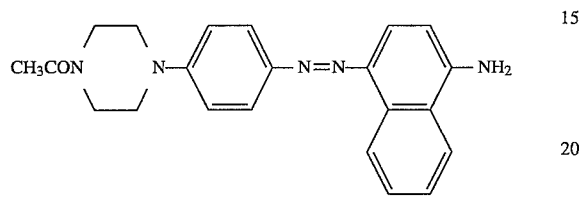
The method of Example 1 Stage (a) was followed except that in place of the 5-amino-2-(4'-acetylpiperazino)benzoic acid there was used 4-(4'-acetylpiperazino)aniline.
(b) Disazo Stage

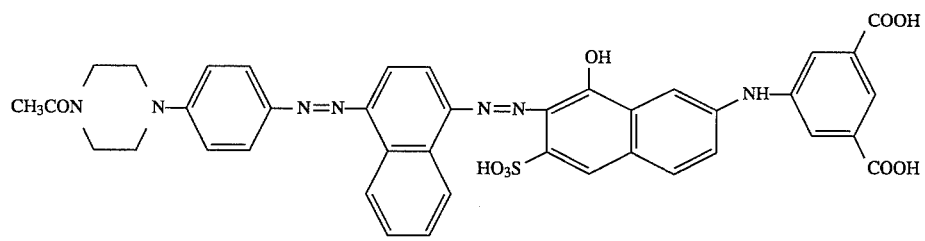

The method of Example 1 stage (b) was followed except that in place of the monoazo product from Example 1, Stage (a), the monoazo product from Example 17, Stage (a) was used and in place of 4-carboxyphenyl-gamma acid there was used 3,5-dicarboxyphenyl gamma acid.

(c) Hydrolysis

The method of Example 2 was used except that in place of the disazo dye used in Example 2 there was used the disazo dye of Example 17, Stage (b). The product was converted to the dry ammonium salt described in Example 2. When made into an ink (2.5% in 90:10 water: 2-pyrrolidone) and printed onto plain paper using a thermal ink jet printer it gave a black image with high waterfastness and good light fastness.

EXAMPLE 18

Preparation of the dye of the Formula (b) Disazo Stage

The method of Example 1, Stage (b) was followed except that in place of the monoazo product from Example 1, Stage (a), the monoazo product from Example 18, Stage (a) was used. The compound of formula (31) was converted to the dry ammonium salt by the method described in Example 2. When made into an ink (2.5% in 90:10 water:2-pyrrolidone) and printed onto plain paper using a thermal ink jet printer it gave a black image with good waterfastness and high light fastness.

EXAMPLE 19

Preparation of the dye of the formula

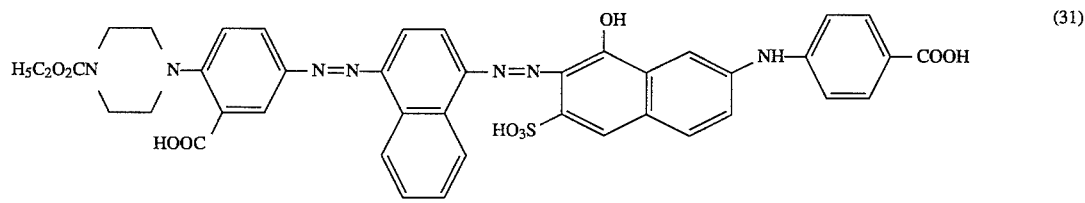
(31)

(a) Monoazo Stage

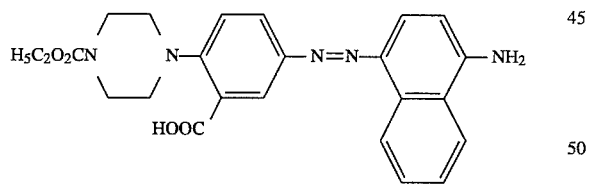

The method of Example 1, Stage (a) was used except that in place of 5-amino-2-(4'-acetylpiperazino)benzoic acid there was used 5-amino-2-(4'-carbethoxypiperazino)benzoic acid.

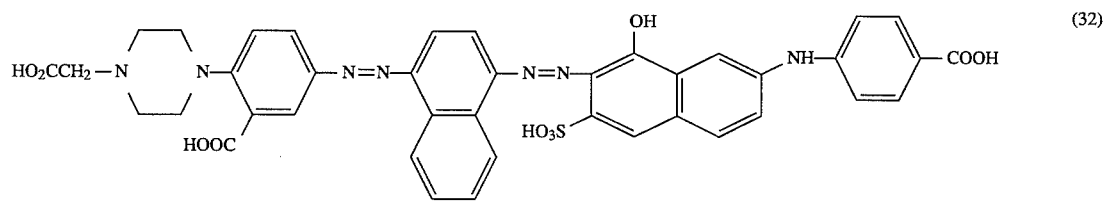
(32)

(a) Monoazo Stage

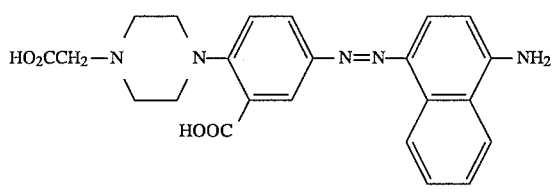

The method of Example 1 Stage (a) was followed except that in place of the 5-amino-2-(4'-acetylpiperazino)benzoic acid there was used 5-amino-2-(4'-carboxymethylpiperazino)benzoic acid.

(b) Disazo Stage

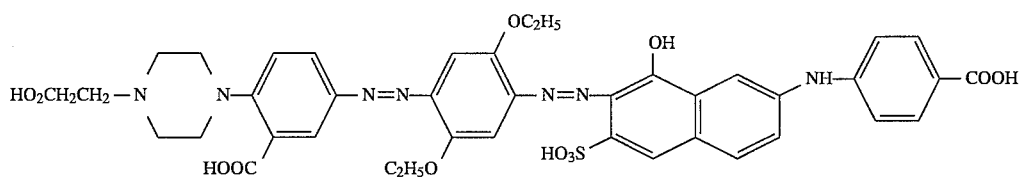

The method of Example 1, Stage (b) was followed except that in place of the monoazo product form Example 1, Stage (a) the monoazo product from Example 19, Stage (a) was used.

The compound of Formula (32) was converted to the dry ammonium salt, by the method described in Example 2. When made into an ink (2.5% in 90:10 water:2-pyrrolidone) and printed onto plain paper using a thermal ink jet printer it gave black images with very high waterfastness and good light fastness.

EXAMPLE 20

In place of the 2,5-dimethoxylaniline used in Example 11 there can be used an equivalent amount of 2,5-diethoxyaniline to give the dye of formula

EXAMPLE 21

In place of the 3-amino-4-methoxy-acetanilide used in Example 12 there can be used an equivalent amount of 3-amino-4-ethoxyacetanilide to give the dye of formula

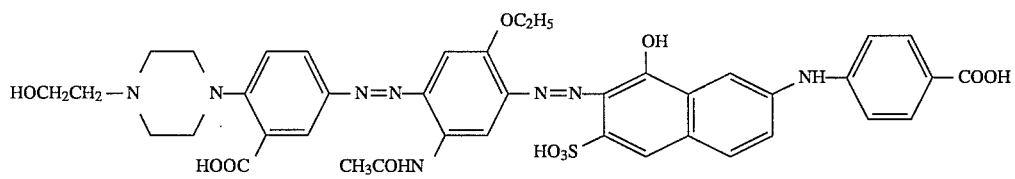

EXAMPLE 22

In place of the 5-amino-2-(4'-methyl-piperazino)benzoic acid used in Example 6 there can be used an equivalent amount of 5-amino-2-(4'-ethylpiperazino)benzoic acid to give the dye of the formula

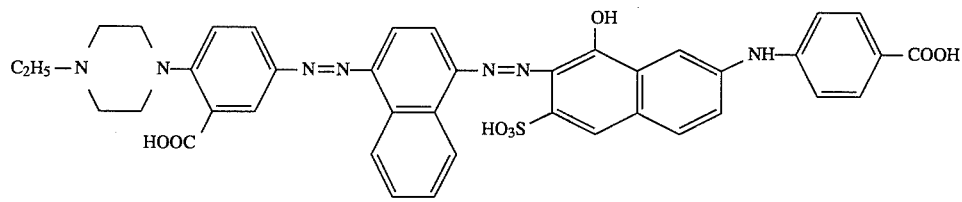

EXAMPLE 23

In place of the 5-amino-2-(4'-(2'-hydroxyethyl)-piperazino)benzoic acid used in Example 5 there may be used an equivalent amount of 5-amino-2-(4'-(2'-hydroxyethoxy)ethyl piperazino)benzoic acid to give the dye of Formula.

EXAMPLE 26

In place of the 5-amino-2-(4'-acetyl-3-methylpiperazino)benzoic acid used in Example 3 there may be used an equivalent amount of 3-amino-4-(4'-acetyl-3-methyl-piperazino)benzoic acid to give the dye of formula.

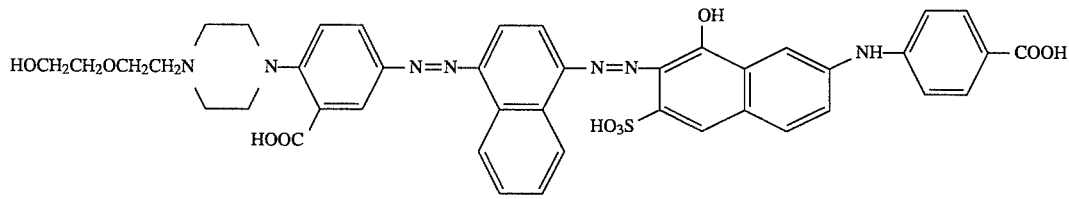

EXAMPLE 24

In place of the 5-amino-2-(4'-methyl-piperazino)benzoic acid used in Example 6 there may be used an equivalent amount of 5-amino- 2-(4'-benzylpiperazino)benzoic acid to give the dye of formula.

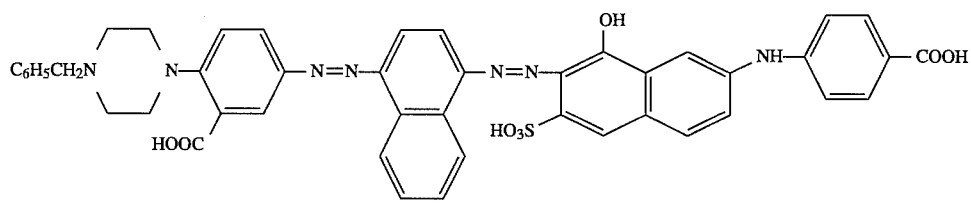

EXAMPLE 25

In place of the 5-amino-2-(4'-methyl-piperazino)benzoic acid used in Example 6 there may be used an equivalent amount of 5-amino-2-(4'-(2"-cyanoethyl)-piperazino)benzoic acid to give the dye of formula.

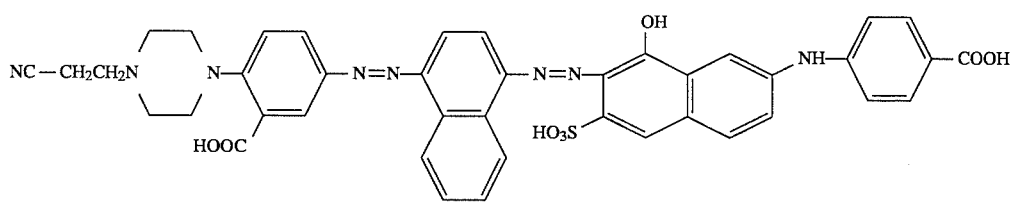

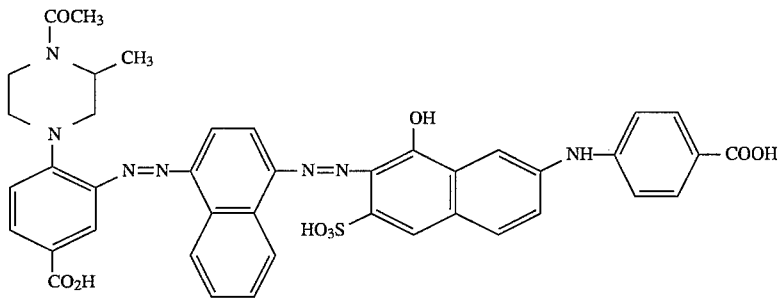

EXAMPLE 27

In place of the 5-amino-2-(3'-methyl-piperazino)benzoic acid used in Example 4 there may be used an equivalent amount of 5-amino-2-(3',5'-dimethylpiperazino)benzoic acid to give the dye of formula.

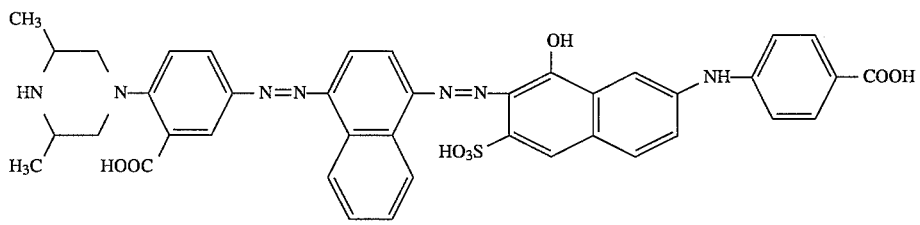

EXAMPLE 28

Preparation of the dye of formula

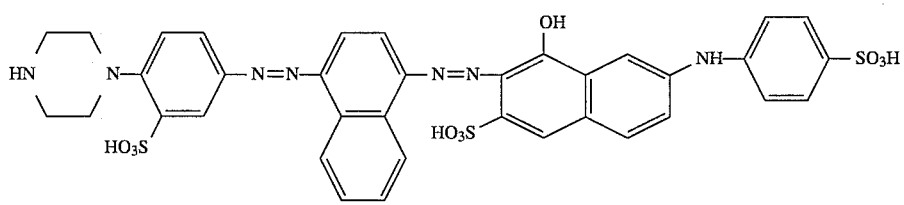

In place of the 5-amino-2-(4'-acetylpiperazino)benzoic acid used in Example 1 there may be used an equivalent amount of 5-amino- 2-(4'-acetyl-piperazino)benzene sulphonic acid. The acylated product is then hydrolysed by the method of Example 2.

Each of the dyes disclosed in Examples 20 to 28 will give a strong black image when converted into an ink (2.5% in 90:10 water: 2-pyrrolidone) which will exhibit good light and water fastness Examples of specific liquid media which can be used to prepare inks containing the dyes disclosed in Examples 1 to 28 and other Colorants within the scope of the present invention are:

Water (60); Ethylene glycol (40)
Water (85); Diethylene glycol (15)
Water (90); Diethylene glycol (10)
Water (65); Glycerol (25); Triethanolamine (10)
Water (80); Ethylene glycol (15); Polyethylene glycol, MW 200 (5)
Water (80); Ethylene glycol (15); N-Methylpyrrolidone (5)
Water (80); Ethylene glycol (15); 2-Pyrrolidone (5)
Water (90); 2-Pyrrolidone (10)

We claim:

1. A compound of Formula (1) or a salt thereof:

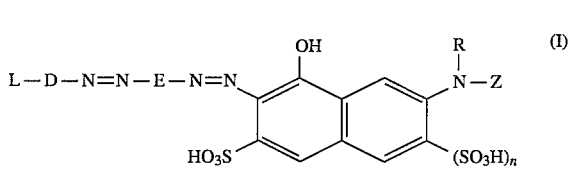

wherein:
L is optionally substituted piperazinyl;
D is optionally substituted phenylene or naphthylene;
E is optionally substututed phenylene, naphthylene or quinolinylene;
R is H or $C_{1-4}$-alkyl;
Z is optionally substituted carboxyaryl; and
n has a value of 0 or 1.

2. A compound according to claim 1 wherein the group represented by L—D- is of the Formula (3) or (4):

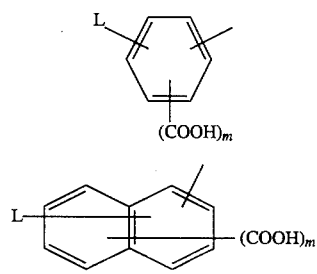 (3)

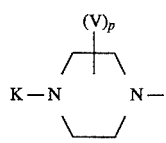 (4)

wherein m is 0 or 1; and

L is of Formula (2)

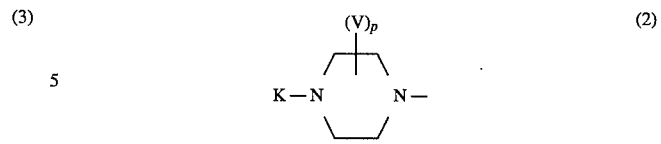 (2)

wherein:

K is H or optionally substituted alkyl, aryl, acyl or ester radical;

V is optionally substituted alkyl; and p is 0, 1 or 2;

provided that (1) at least one of X and Y is H or COOH and (2) W is C—H or N when X and Y are both COOH.

5. A compound according to claim 1 wherein the optionally substituted piperazinyl group represented by L is of the Formula (2):

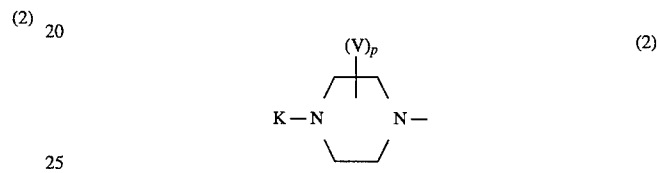 (2)

wherein

K is H or optionally substituted alkyl, aryl, acyl or ester radical;

V is optionally substituted alkyl; and p is 0, 1 or 2.

6. A compound according to claim 5 wherein the piperazinyl group is selected from the group consisting of piperazin-1-yl, 4-hydroxyethylpiperazin-1-yl, 4-acetyl-piperazin-1-yl, 3-methylpiperazin-1-yl, 3-methyl-4-acetyl-piperazin-1-yl, 4-formylpiperazin-1-yl and 4-methylpiperazin-1-yl.

in which p is 0 or 1; V is CH$_3$ or OCH$_3$; and K is selected from the group consisting of H, C$_{1-4}$-alkyl; formyl; C$_{1-4}$-alkyl-carbonyl; phenylcarbonyl; an ester radical; and hydroxy-C$_{1-4}$-alkyl.

3. A compound according to claim 2 wherein K is methyl, C$_{1-4}$-alkoxycarbonyl, phenoxycarbonyl or hydroxyethyl.

4. A compound of Formula (5) or a salt thereof:

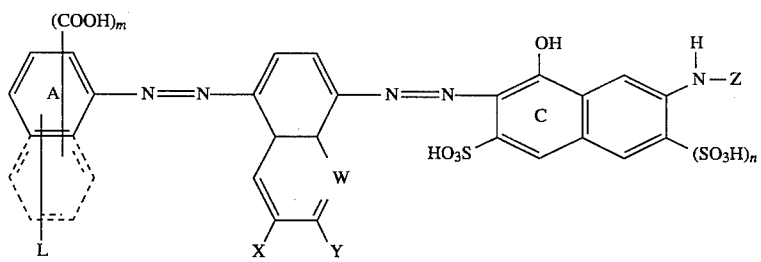 (5)

wherein n has a value of 0 or 1;

W is C—H, C—COOH or N;

X and Y each independently is H, COOH or SO$_3$H;

m is 0 or 1;

Z is optionally substituted carboxy aryl; and

L is of the Formula (2):

7. A compound according to any one of claims 1 to 6 wherein Z is selected from the group consisting of 3-carboxyphenyl, 4-carboxyphenyl and 3,5-dicarboxyphenyl.

8. A compound according to any one of claims 1 to 6 in the form of an ammonium or substituted ammonium salt.

* * * * *